US00PP23068P3

(12) United States Plant Patent
Sykes

(10) Patent No.: US PP23,068 P3
(45) Date of Patent: Sep. 25, 2012

(54) MANDARIN TREE NAMED 'MERBEINGOLD 2336'

(50) Latin Name: *Citrus reticulata×(C. reticulata×C. sinensis)*
Varietal Denomination: Merbeingold 2336

(75) Inventor: Stephen Richard Sykes, Mildura (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 12/927,626

(22) Filed: Nov. 19, 2010

(65) Prior Publication Data

US 2011/0078836 P1 Mar. 31, 2011

Related U.S. Application Data

(63) Continuation of application No. 11/729,003, filed on Mar. 27, 2007, now abandoned.

(30) Foreign Application Priority Data

Oct. 16, 2006 (AU) ..... PBR 2006279

(51) Int. Cl.
*A01H 5/00* (2006.01)

(52) U.S. Cl. ..... Plt./202

(58) Field of Classification Search ..... Plt./202
See application file for complete search history.

(56) References Cited

U.S. PATENT DOCUMENTS

2008/0127378 P1 5/2008 Sykes
2008/0127379 P1 5/2008 Sykes
2011/0107481 P1 5/2011 Sykes

OTHER PUBLICATIONS

Acceptance of Merbeingold 2336, Application No. 2006/279, for Plant's Breeder's Right Registration on Dec. 1, 2006. Published in Plant Varieties Journal, 2007 19(4), Canberra; Australian Government Publishing Service, Australia.
Complete file history for U.S. Patent Publication No. 2008-0127378 P1, published May 29, 2008 (Stephen Richard Sykes) (issued from U.S. Appl. No. 11/729,003).

*Primary Examiner* — Annette Para
(74) *Attorney, Agent, or Firm* — John P. White; Cooper & Dunham LLP

(57) ABSTRACT

'Merbeingold 2336' is a new Australian variety of mandarin. It was selected from the progeny obtained following a controlled pollination of 'Imperial' mandarin×'Ellendale' tangor in 1984. It was selected because it is pollen sterile, strongly parthenocarpic and yields seedless fruits, which are sweet, juicy and easy-to-peel. Fruit maturity is early-to-mid season in the Murray Valley of Australia. Internally, the flesh of 'Merbeingold 2336' is attractive, orange in colour and tender with soft segment walls.

4 Drawing Sheets

Latin name of the genus and species of the plant claimed: *Citrus reticulata*×(*C. reticulata*×*C. sinensis*).

Variety denomination: 'Merbeingold 2336'.

'Merbeingold 2336' was accepted for Plant Breeder's Right ("PBR") registration on Dec. 1, 2006 when a provisional PBR was granted. Acceptance was published in the Plant Varieties Journal (2007) Vol. 19, No 4, p23 (see, ipaustralia.gov.au/pdfs/plantbreed/PVJ_19_4.pdf). The Commonwealth of Australia Plant Breeder's Rights Act 1994 follows the guidelines of the International Convention for the Protection of New Varieties of Plants—UPOV Convention (1961), as revised at Geneva (1972, 1978 and 1991). Australia is a UPOV Member State.

BACKGROUND OF THE INVENTION

'Merbeingold 2336' is a new variety of mandarin (*Citrus* species) bred by CSIRO Plant Industry. A copending application, U.S. Ser. No. 11/729,049, has been made for the variety 'Merbeingold 2350', which is a sibling selected from the same family as 'Merbeingold 2336'.

'Merbeingold 2336' is a mandarin variety selected from a family produced by making a controlled cross between 'Imperial' mandarin (seed parent) with 'Ellendale' tangor (pollen parent). Thus, the botanical name for the plant is:

*Citrus reticulata*×(*C. reticulata*×*C. sinensis*)

The plant was asexually reproduced in South Australia, Australia.

'Merbeingold 2336' was selected from a family of 241 hybrids generated by a controlled cross-pollination of 'Imperial' mandarin (maternal parent) with 'Ellendale' tangor (pollen parent).

'Imperial' mandarin (unpatented) is an Australian variety that originated at Emu Plains, NSW, as a chance seedling in 1890. It is possibly a hybrid of the 'Mediterranean' mandarin. 'Imperial' trees are vigorous, upright and of medium size and they yield fruits that are early maturing.

'Ellendale' tangor (unpatented) is another Australian variety that was discovered as a chance seedling at Burrum, Queensland in 1878. Although its parentage is unknown, its characteristics and fruit size indicate that it is a tangor (mandarin×orange cross). 'Ellendale' trees are generally large and of a spreading-round habit and produce large mid-to-late season fruit depending on where they are grown.

The seediness of fruits from both 'Imperial' and 'Ellendale' can be variable ranging from many-to-few-to-zero depending on the proximity of other sources of pollen. Both varieties are capable of producing fruits parthenocarpically.

CSIRO Plant Industry crossed 'Imperial' with 'Ellendale' to combine the characteristics of the two varieties and generate new parthenocarpic hybrids for selection of potential new varieties of seedless mandarins.

The controlled cross-pollination was conducted by emasculating an un-opened flower bud of the maternal parent and applying pollen from the paternal parent to the receptive stigma using a sterile soft-haired paintbrush. Pollen of 'Ellendale' tangor was collected by drying anthers, which had been removed from unopened flower buds, in Petri dishes over silica gel in a dessicator. Dried dehisced anthers were stored in sealed glass vials over silica gel at 4° C. until needed. The cross was made in 1984 and the resultant seeds were extracted from fruits in 1985 and sown in a standard seed bed under glasshouse conditions. Emergent seedlings were transferred to a standard potting mix in pots and maintained under glasshouse conditions until they were rowed out in the breeding orchard at a planting density of 2 m within and 6 m between rows. Hybrid seedlings were maintained under irrigated orchard conditions thereafter. Standard citrus cultivation techniques were used to maintain the trees including application of fertilisers.

When hybrid 2336 flowered, it was subjected to a range of pollination treatments to assess its potential for producing seedless fruits. Fruits were harvested over 4 years and assessed for fruit quality, Based on the data collected, hybrid 2336 was selected for entry into second phase evaluation trials.

The selection was entered into a comparative trial at CSIRO Plant Industry Koorlong (NW Victoria). Trees of hybrid 2336 and 4 comparator varieties (viz. 'Clementine Nules', 'Imperial' mandarin, 'Ellendale' tangor, and 'Merbeingold 2350') were propagated by budding to 3 rootstocks (viz. 'Carrizo' citrange, 'Cleopatra' mandarin and 'Symons' sweet orange) in the nursery at CSIRO. The DUS trial was planted during spring 2001. The soil type was classified as being Tiltao sand (Northcote, K.H. 1951. A Pedological Study of the Soils Occurring at Coomealla, New South Wales, Commonwealth Scientific and Industrial Research Organisation, Melbourne, Australia). The trees were irrigated by overhead sprays and fertilised using a standard citrus N:P:K (12:3:3) formulation. Fertiliser was applied to young trees at 2-monthly intervals and to trees 2 years and older at six-monthly intervals at a rate such that they received 800 kg/ha/year. Trace elements, primarily manganese and zinc were applied as foliar sprays as required. The trial was embedded within a larger trial that compared other selections from CSIRO's citrus breeding program. The trial was laid out as two randomized blocks with a three-tree plot for every scion/rootstock combination within each block. Rootstocks were randomized within plots. Trees were maintained vegetatively for the first three years and allowed to retain fruits from season 2004-05 onwards.

Comparative data for quantitative fruit characteristics were collected in seasons 2006 and 2007. Spring-flush leaves were sampled from trees during January 2007.

Hybrid 2336 was also entered along with other selections into regional test plots with anonymous cooperating citrus growers under confidential testing agreement arrangements to protect inherent intellectual property. Based on its performance in these trials and test plots, hybrid 2336 was named 'Merbeingold 2336'.

Daughter trees of 'Merbeingold 2336' propagated from the original seedling tree by asexual or vegetative means are uniform and stable. Similarly grand-daughter trees are uniform and stable. Trees of 'Merbeingold 2336' have been propagated by grafting or budding to seedling rootstocks, by top-working to established orchard trees and by rooting cuttings, confirming its uniformity and stability.

BRIEF SUMMARY OF THE INVENTION

Fruits of 'Merbeingold 2336' are seedless even when challenged by viable pollen in an open-pollinated situation. The fruits are easy-to-peel and upon peeling, the segments are readily separated although some albedo tissue may adhere to the segments. Peeled segments are very tender with relatively soft walls meaning they are easy to consume and as a result the fruit has been described as melting. The juice has a ° Brix of around 10 and an acid concentration of less than 1% at maturity, which gives a sweet flavour. The flavour and soft, easy-eating texture of the segments are favoured by children.

The colour of the rind and the flesh, like 'Clementine Nules' and 'Ellendale' is medium orange, while the rind and flesh of 'Imperial' is yellow orange. Thus, though more orange than red-orange, the colour of the rind and flesh is more intense than 'Imperial' mandarin. The color of the albedo is white like each of 'Clementine Nules', 'Ellendale', and 'Imperial'. Like 'Imperial' mandarin, rind strength is not high, which suggests the fruit may be more suited for domestic sales rather than shopping to more distant export markets.

Large fruits tend to be puffy, although cultural practices such as GA sprays have a positive effect to reduce this and improve rind quality. Fruits of 'Merbeingold 2336' can be snapped from the tree, but care should be taken as the button will be removed if harvesting is too violent. Fruits of 'Merbeingold 2336' are mature in the period June-through-July in Australia's Murray Valley, although the exact time for optimum quality will depend on rootstock and season. The range in fruit size tends to be similar to that of 'Imperial' mandarin.

DETAILED BOTANICAL DESCRIPTION

Variety: 'Merbeingold 2336' *Citrus reticulata*×(*C. reticulata*×*C. sinensis*).

Descriptors used herein from 1) European Union Community Plant Variety Office, Protocol for distinctness, uniformity and stability tests. *Citrus* L.—Group 1 MANDARINS. CPVO-TP\201\1 Adopted 18 Nov. 2004, and 2) IPGRI (1999) Descriptors for *Citrus*. International Plant Genetic Resources Institute, Rome, Italy (ISBN 92-9043-425-2).

Plant: Diploid, growth habit spreading-to-upright, tree shape spheroid, density of branches medium, branch angle narrow, trunk surface smooth, shoot tip green and surface glabrous. Compared to the varieties 'Clementine Nules', 'Ellendale', and 'Imperial', the tree has a spreading growth habit, like 'Ellendale', but unlike 'Clementine Nules' which has a drooping growth habit, and 'Imperial' which has an upright growth habit. Additionally, the tree has very short spines, compared to 'Clementine Nules', 'Ellendale', and 'Imperial', which each have short spines.

The height and spread of 3 trees of 'Merbeingold 2336' were measured. These trees had been planted as nursery-propagated trees (12 months from budding) in April 2000 and were 12 years-old when measured. Intra- and inter-row spacing was 2 m and 6 m, respectively. North-south and east-west diameters of the 'Merbeingold 2336' trees ranged from 4000-to-4100 mm and 4200-to-4400 mm, respectively. The height of the 'Merbeingold 2336' trees ranged between 4000-to-4200 mm. The Royal Horticultural Society (R.H.S.) colour chart data provided herein were collected from the same trees used for height and spread measurement.

Figure 1A:
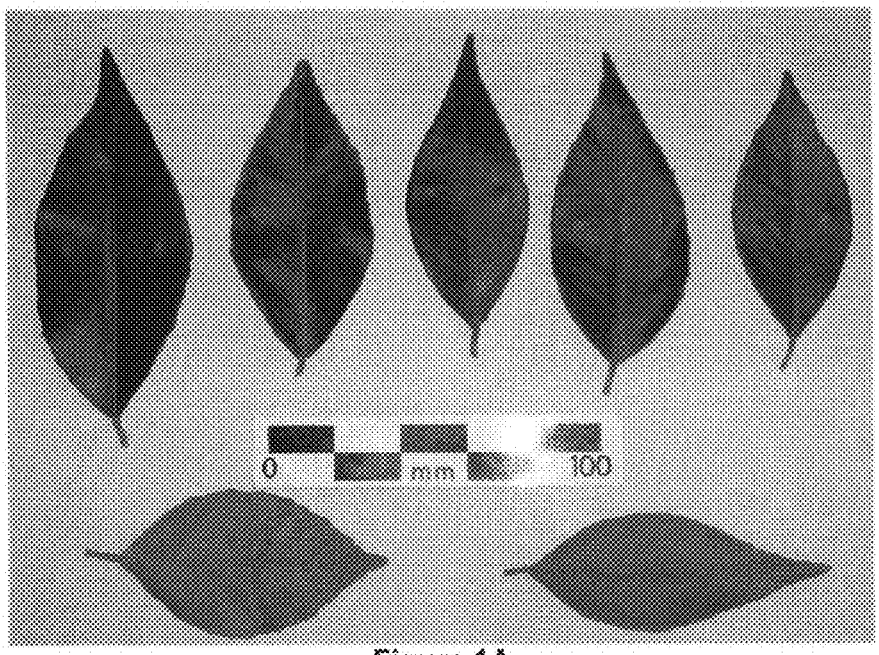
FIGS. 1A-1C: Show leaves from 'Merbeingold 2336' (FIG. 1A) and its parents, 'Imperial' mandarin (FIG. 1B) and 'Ellendale' tangor (FIG. 1C). In 'Merbeingold 2336' the Lamina length:width ratio=2.2±0.3; in 'Imperial' mandarin the Lamina length:width ratio=2.7±0.2; and in 'Ellendale' tangor the Lamina length:width ratio=2.1±0.2
Figure 1B:
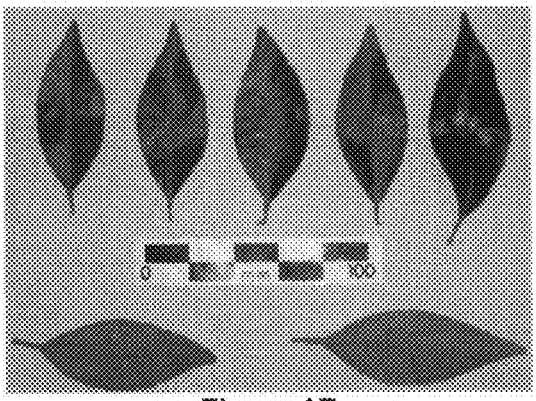
Figure 1C:
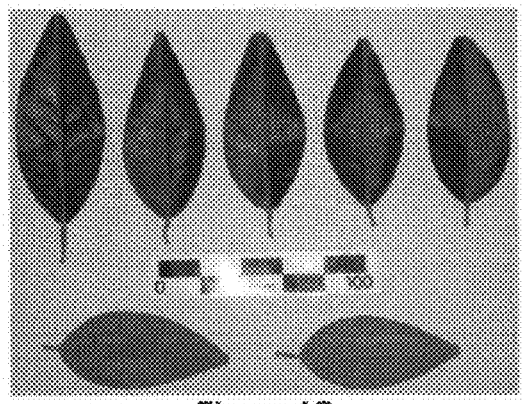
Figure 2A:
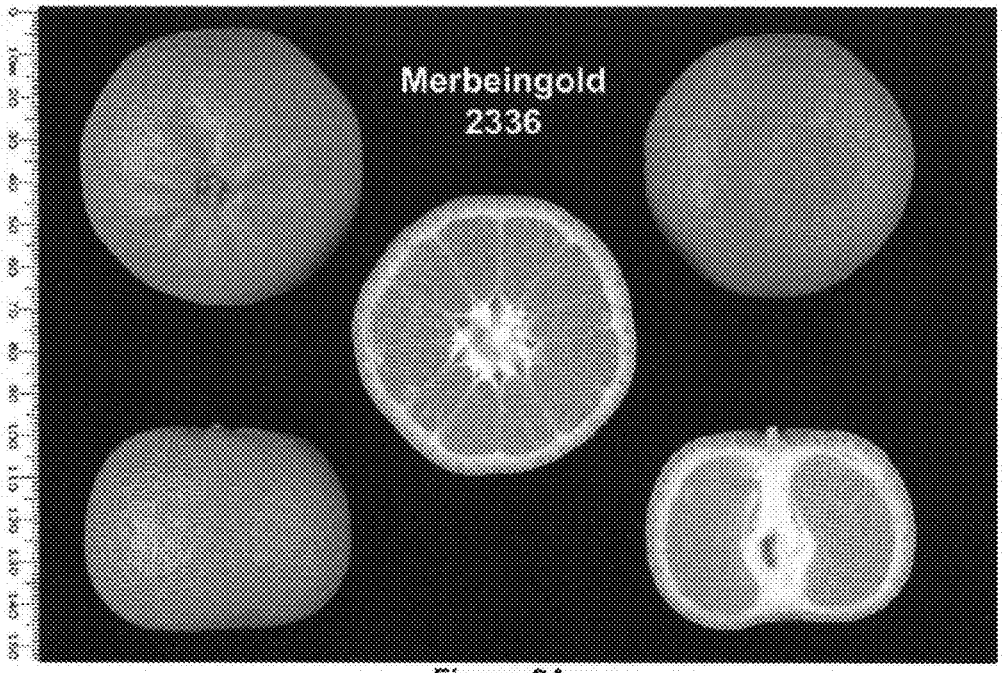
FIGS. 2A-2C: Show fruit of 'Merbeingold 2336' (FIG. 2A) and its parents, 'Imperial' mandarin (FIG. 2B) and 'Ellendale' tangor (FIG. 2C).
Figure 2B:
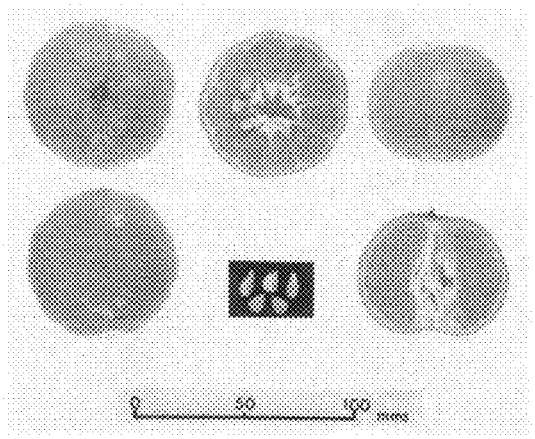
Figure 2C:
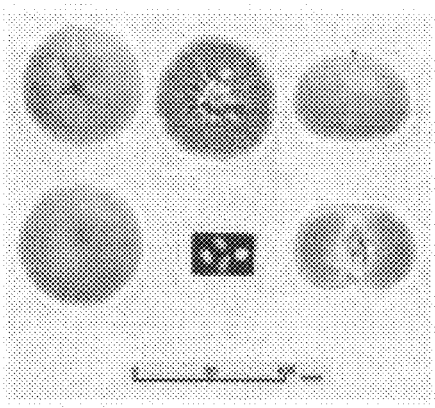
Figure 3:
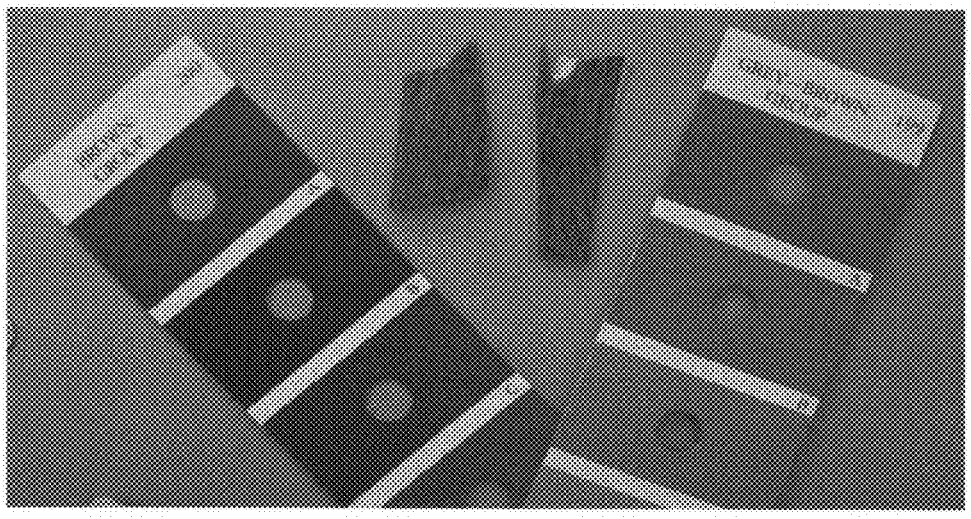
FIG. 3: A. Shows the colour of bark of the 'Merbeingold 2336' tree. B. Shows the colour of leaves of the 'Merbeingold 2336' tree. C. Shows the colour of fruit of the 'Merbeingold 2336' tree.
Figure 3:
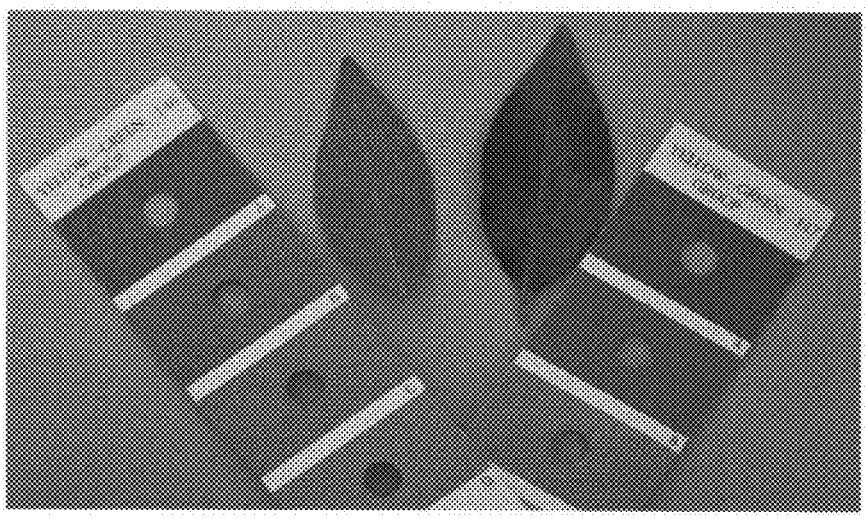
Figure 3:
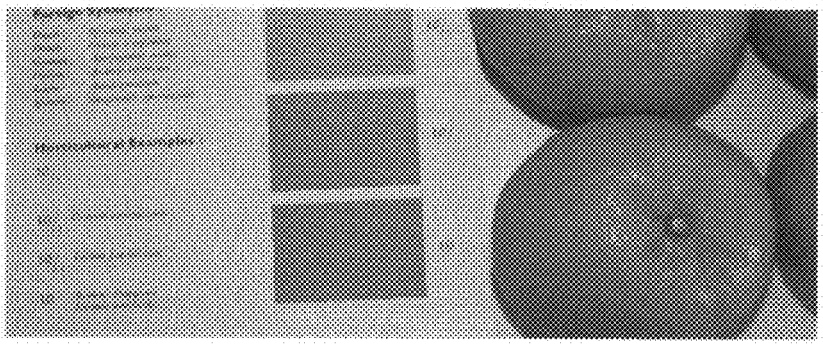
Figure 4:
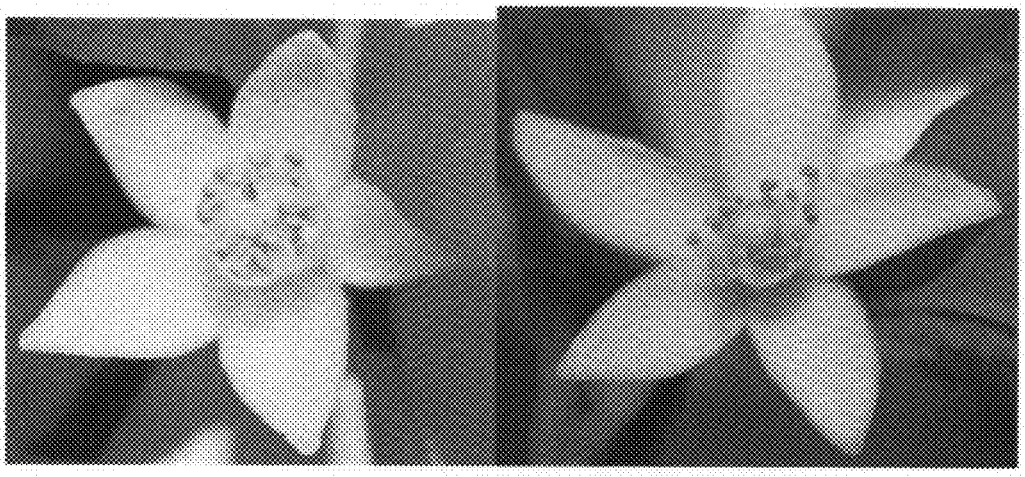
FIG. 4: Shows flowers of the 'Merbeingold 2336' tree.

Bark samples were removed from a central leader within the canopy and colour scored away from the tree under conditions suggested by the R.H.S. chart document. The bark was streaked as shown in FIG. 3A and was thus scored as being brown-grey (200) to grey brown (199) with bands represented by these colour types.

Spine (thorn): Absent on adult tree.

Leaf: Evergreen, type simple, shape ovate, intensity of green colour on lamina medium-to-dark, colour variegation absent, margin weakly dentate, shape of apex acute, length medium (91±11 mm), lamina width broad (42±6 mm), lamina length to width ratio 2.2±0.3, cross-sectional shape intermediate, lamina undulation slight, lamina attachment brevipetiolate, petiole length short (10±3), petiole wings obdeltate and very narrow, petiole attachment to stem curved, junction between petiole and lamina articulate, colour of upper/lower surface of lamina same. The colour of the leaves may be characterized as dark to very dark green, like the 'Clementine Nules', 'Ellendale', and 'Imperial' varieties.

The upper (adaxial) surface was scored as 147a from the yellow-green group; the lower (abaxial) surface was scored as 146a from the yellow-green group of The R.H.S. Color Chart (FIG. 3B).

Flower: Hermaphrodite, arrangement solitary and as a raceme, position axillary and terminal, length of petal medium, anther colour pale yellow-to-white, viable pollen absent, length of anther relative to style shorter (inferior), colour of open flower white like the 'Clementine Nules', 'Ellendale', and 'Imperial' varieties, 5 petals per flower, stamens >4 per petal, style straight and complete, self-pollen reaction sterile.

Fruit: Maturity early-to-mid-season (June Australia), borne both inside and outside canopy, obloid, attachment to stalk medium-to-strong, broadest at equator, shape in transverse section circular, base truncate, apex depressed slightly, neck absent, slight depression at stalk end, number of radial grooves at stalk end intermediate, collar absent, distal part slightly concave-to-flattened, depression at distal end, areola absent, stylar end closed, stylar scar small, style not persistent, navel opening absent, radial grooves at distal end absent, rind surface orange, surface glossiness strong, rind surface smooth-to-very slightly pitted, oil glands all more-or-less same size, slight pitting of oil glands present pebbling absent, oil glands very weakly conspicuous, small and of low density, rind thickness medium (3-5 mm), rind adherence to flesh weak, rind strength medium, rind oiliness dry, albedo white and loose, amount of albedo adhering to flesh small-to-medium, albedo strands present, flesh medium orange, pulp colour uniform, pulp firmness soft, pulp texture fleshy, core medium, round and sparsely filled, segments uniform, rudimentary segments absent, number of well developed segments medium (7-12; mean 9.5±1.7), adherence of segment walls to each other medium, segment walls thin and weak, vesicle length medium, vesicle thickness medium, navel absent, juiciness medium-to-high, total soluble solids medium 9-11 ° Brix, juice acidity low-to-medium, strength of fibre weak, parthenocarpy present.

The color of the rind of fruit from the 'Merbeingold 2336' tree is Orpiment Orange 10-10/1 in The R.H.S. Colour Chart (FIG. 3C).

It will be understood that the average size of fruits will vary with location, season, rootstock, nutrition, irrigation, crop load etc. The data provided in Table 1 are for the 'Merbeingold 2336' tree grown in a semi-commercial planting. The trees were top-worked in January 2006 in Australia.

Fruit weight and diameter of 'Merbeingold 2336' fruit determined from a random sample of fruit taken from a fruit bin at harvest of top-worked trees in the semi-commercial sized trial. Data are means ± standard deviations for sample sizes that varied according to year.

| Variety | Harvest date | Fruit weight (g) | Fruit diameter (mm) |
|---|---|---|---|
| Merbeingold 2336 | Jun. 6, 2008 | 135.4 ± 6.7 | 67.8 ± 2.2 |
| | Jun. 10, 2009 | 120.9 ± 24.8 | |
| | Jun. 10, 2010 | 146.3 ± 20.0 | |
| | Jun. 14, 2011 | 104.0 ± 25.9 | 61.2 ± 6.2 |

Missing values are where these data were not recorded.

Seed: Number zero under controlled manual self pollination, or 0-3 (mostly 0) under open-pollination dependent on proximity of pollen sources, monoembryonic, shape ovoid, length short, width narrow, surface smooth, external colour whitish/cream, colour of inner seed coat light brown, chalazal cream, cotyledons white-to-light yellow-cream.

What is claimed is:

1. A new and distinct pollen sterile, parthenocarpic mandarin tree named 'Merbeingold 2336' as illustrated and described.

* * * * *

A

B

C